: US 8,419,660 B1
(45) Date of Patent: Apr. 16, 2013

(12) United States Patent
Shaw

(10) Patent No.

(54) PATIENT MONITORING SYSTEM

(75) Inventor: Mark Shaw, Poland, OH (US)

(73) Assignee: Primus Medical, Inc., Youngstown, OH (US)

( * ) Notice: Subject to any disclaimer, the term of this patent is extended or adjusted under 35 U.S.C. 154(b) by 2303 days.

(21) Appl. No.: 11/145,491

(22) Filed: Jun. 3, 2005

(51) Int. Cl.
*A61B 5/103* (2006.01)

(52) U.S. Cl.
USPC .......................................... 600/595; 600/587

(58) Field of Classification Search ............... 600/595, 600/300, 301, 534, 535, 549, 587; 601/152
See application file for complete search history.

(56) References Cited

U.S. PATENT DOCUMENTS

| 3,781,843 | A | 12/1973 | Harrison et al. ............... 340/279 |
| 4,003,374 | A | 1/1977 | Mizrachy ........................... 128/48 |
| 4,020,428 | A | 4/1977 | Friend et al. ...................... 333/73 |
| 4,175,263 | A | 11/1979 | Triplett et al. .................. 340/573 |
| 4,401,896 | A | 8/1983 | Fowler et al. ................... 307/118 |
| 4,539,560 | A | 9/1985 | Fleck et al. ...................... 340/573 |
| 4,624,244 | A | 11/1986 | Taheri ............................... 128/24 |
| 4,907,845 | A | 3/1990 | Wood ............................... 340/573 |
| 4,987,783 | A * | 1/1991 | D'Antonio et al. ........... 73/432.1 |
| 4,994,793 | A | 2/1991 | Curtis ............................. 340/666 |
| 5,140,309 | A | 8/1992 | Gusakov ........................ 340/573 |
| 5,276,432 | A | 1/1994 | Travis ............................. 340/573 |
| 5,328,445 | A | 7/1994 | Spahn et al. ...................... 602/13 |
| 5,353,012 | A | 10/1994 | Barham et al. ................. 340/573 |
| 5,443,440 | A | 8/1995 | Tumey et al. ................... 601/152 |
| 5,453,082 | A | 9/1995 | Lamont ........................... 602/27 |
| 5,561,412 | A | 10/1996 | Novak et al. ............. 340/286.07 |
| 5,699,038 | A | 12/1997 | Ulrich et al. ............. 340/286.07 |
| 5,780,798 | A | 7/1998 | Hall-Jackson ................... 200/85 |
| 5,808,552 | A | 9/1998 | Wiley et al. .................... 340/573 |
| 5,838,223 | A | 11/1998 | Gallant et al. ........... 340/286.07 |
| 6,010,468 | A | 1/2000 | Grove et al. ...................... 601/23 |
| 6,067,019 | A | 5/2000 | Scott .......................... 340/573.4 |
| 6,147,592 | A | 11/2000 | Ulrich et al. ............... 340/286.7 |
| 6,208,250 | B1 | 3/2001 | Dixon et al. ............... 340/573.1 |
| 6,252,512 | B1 | 6/2001 | Riley ............................. 340/665 |
| 6,362,725 | B1 | 3/2002 | Ulrich et al. ............... 340/286.7 |
| 6,373,392 | B1 * | 4/2002 | Au ............................. 340/573.1 |
| 6,375,633 | B1 | 4/2002 | Endress et al. .................. 602/23 |
| 6,438,776 | B2 | 8/2002 | Ferrand et al. .................... 5/600 |
| 6,439,264 | B1 | 8/2002 | Ellis et al. .................. 137/596.2 |
| 6,694,556 | B2 | 2/2004 | Stolpmann ........................ 5/710 |
| 6,702,768 | B2 | 3/2004 | Mano et al. ...................... 601/29 |
| 6,755,798 | B2 | 6/2004 | McCarthy et al. .............. 602/13 |
| 6,813,790 | B2 | 11/2004 | Flick et al. ........................ 5/713 |
| 2003/0216670 | A1 * | 11/2003 | Beggs ............................. 600/595 |
| 2005/0154336 | A1 * | 7/2005 | Kloecker et al. .............. 601/148 |
| 2005/0172405 | A1 * | 8/2005 | Menkedick et al. .............. 5/618 |
| 2006/0258964 | A1 * | 11/2006 | Biondo et al. ................. 601/152 |

* cited by examiner

*Primary Examiner* — Jeffrey G Hoekstra
*Assistant Examiner* — Fangemonique Smith
(74) *Attorney, Agent, or Firm* — Shannon V. McCue; Hahn Loeser & Parks LLP

(57) ABSTRACT

A patient monitoring system including a migration sensor that includes a compressible member that defines a chamber at least partially filled with fluid and a pressure sensor in fluid communication with the member. The member is attached to the mattress at a selected location to detect movement of the patient. The monitoring system includes a controller that monitors the pressure sensor, and is adapted to notify a care giver upon detecting a selected pressure change within the member.

2 Claims, 2 Drawing Sheets

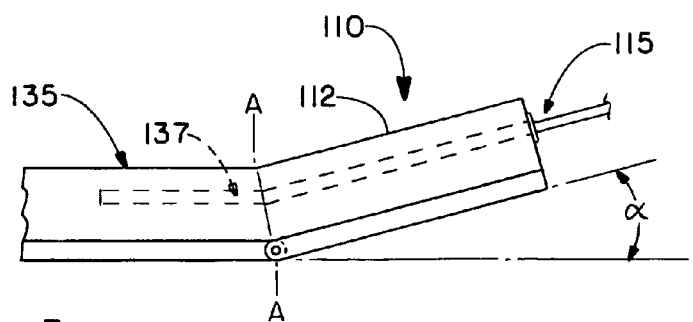
FIG.-5
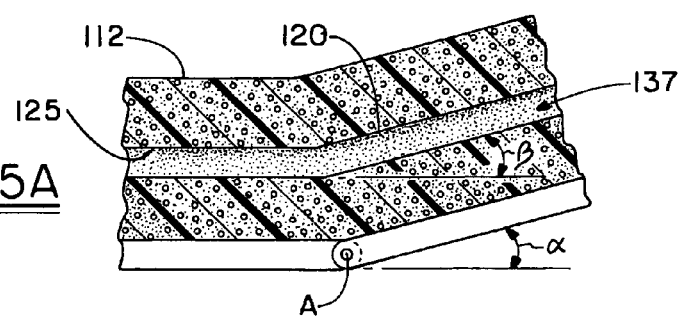
FIG.-5A
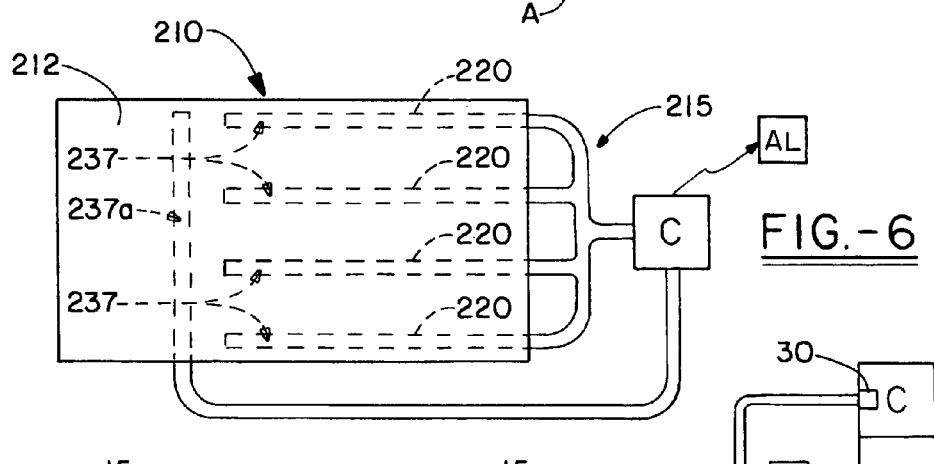
FIG.-6
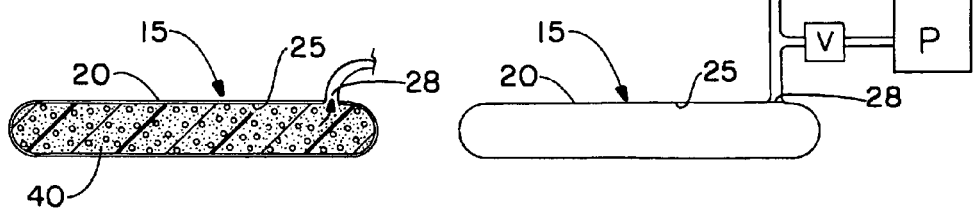
FIG.-7
FIG.-8

PATIENT MONITORING SYSTEM

TECHNICAL FIELD

The present invention generally relates to a patient monitoring system that detects forces to monitor migration of the patient. More particularly, the present invention relates to a system including a compressible member that defines a chamber fluidly connected to a pressure sensor to detect migration forces through changes in the member's pressure.

BACKGROUND OF THE INVENTION

In patient care, one concern is the possibility that a patient will fall out of bed or chair, or attempt to exit a bed or chair before they are able and injure themselves or otherwise move to a position that compromises their care or safety, for simplicity these conditions will be collectively referred to as a "dangerous condition" herein. Consequently, extensive efforts have been made to monitor a patient's position and prevent them from falling or exiting without care giver supervision. Efforts have been made to prevent such dangerous conditions from occurring by alerting the care giver.

One method includes attaching a string to the patient's clothing and connecting the string to an alarm. Once a threshold tension on the string is achieved, i.e., when the patient moves beyond the range of motion permitted by the string, an alarm sounds alerting care givers. As will be appreciated, this system is limited to warning the care giver only after the patient has moved beyond the permissible range, and, thus, may only warn a care giver after the patient has gotten out of or fallen from the bed.

Another known system employs multiple load cells, within the bed frame, that are located at positions around the patient to determine the patient's center of gravity at any given moment. In this way, the patient's position may be accurately monitored providing warning to a remote care giver as the patient approaches a dangerous position. In this way, the system may prevent a fall by providing earlier warning to the care giver.

SUMMARY OF THE INVENTION

The present invention generally provides a patient monitoring system including a migration sensor that includes a compressible member that defines a chamber at least partially filled with fluid and a pressure sensor in fluid communication with the member. The member is attached to the mattress at a selected location to detect movement of the patient. The monitoring system includes a controller that monitors the pressure sensor, and is adapted to notify a care giver upon detecting a selected pressure change within the member.

The present invention further provides a system for monitoring patient migration on a mattress, said system comprising: plural migration sensors, each migration sensor including a member defining a chamber at least partially filled with fluid, said member being compressible, and a pressure sensor in sensing communication with said member; a controller in communication with each pressure sensor, wherein said controller receives a pressure value from said sensor and stores said value in a memory, said controller upon detecting a substantially simultaneous change in the pressure values reported from members on opposite sides of the mattress, being adapted to zero said pressure values in memory.

The present invention further provides a system for monitoring patient migration comprising: a migration sensor that includes a compressible member and a pressure sensor in sensing communication with said compressible member, said compressible member defining a chamber, wherein said pressure sensor is adapted to detect pressure changes within the member; and a controller in communication with said pressure sensor and an alarm, wherein said controller is adapted to receive the detected pressure changes from said

BRIEF DESCRIPTION OF THE DRAWINGS

FIG. 5 is a partially fragmented side elevational view of the mattress depicted in FIG. 4 shown on a pivotable bed frame depicting a portion of the mattress in an elevated position;

FIG. 5a is an enlarged fragmented sectional side elevational view showing details of the migration sensor, when a portion of the mattress is raised;

FIG. 6 is a patient migration monitor according to the concepts of the present invention having an array of migration sensors within the mattress;

FIG. 7 is a partially schematic section side elevational view of a migration sensor according to the concepts of the present invention, where the sensor defines a chamber that has been filled with foam; and FIG. 8 is a partially schematic section side elevational view of a migration sensor according to the concepts of the present invention, where a pump communicates with the sensor's chamber to over inflate the chamber.

DETAILED DESCRIPTION OF THE INVENTION

Figure 1:
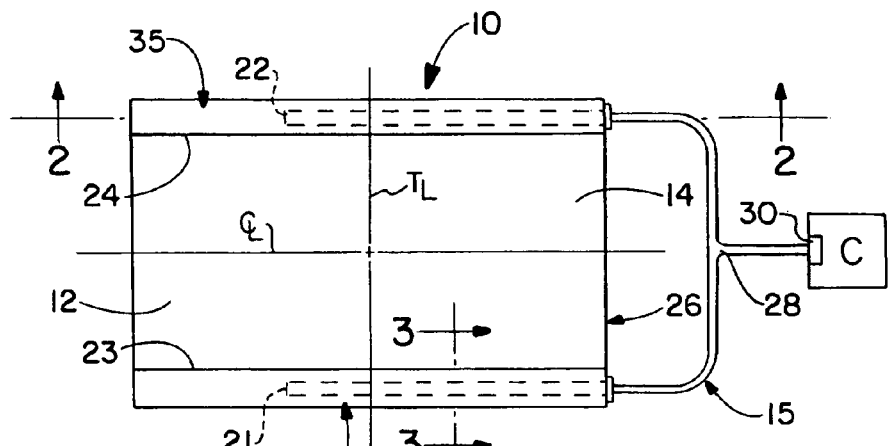
FIG. 1 is a to plan view of the patient migration monitor according to the concepts of the present invention showing a single chamber migration sensor having a pair of insertable ends located near the lateral edges of a mattress.
Figure 2:
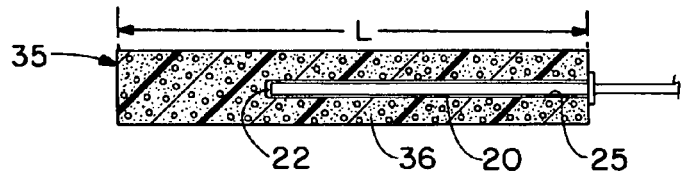
FIG. 2 is a partially fragmented sectional side elevational view, as might be seen along line 2-2 in FIG. 1, depicting details of one insertable end.

The present invention generally provides a patient monitoring system used in connection with a mattress, overlay, cover, cushion, or pad, on which a patient is at least partially supported, collectively referred to herein as a "mattress." The mattress may be used in connection with any supporting frame including, without limitation, a bed, chair, or sofa. More particularly, the present invention relates to a monitoring system that incorporates a migration sensor that includes a member that defines a chamber fluidly connected to a pressure sensor. The migration sensor is placed in proximity to a patient such that movement of the patient applies a force to the member, which is detected by the sensor as a pressure change. Pressure changes are monitored by a controller and reported to a care giver to help alert the care giver of a potentially dangerous condition, for example a patient attempting to exit the mattress or moving to a position where they might fall from the mattress. Use of the terms patient and care giver should be understood as any person and are not limiting. They are merely used to provide context in the sense that a patient is the person being monitored by the care giver. This monitoring could occur in any setting including, for example, hospitals, managed care facilities, emergency shelters, or a home.

One embodiment of a patient monitoring system according to the concepts of the present invention is shown, as an example, in the drawings and generally indicated by the numeral 10. System 10 includes a migration sensor, generally indicated by the numeral 15. Migration sensor includes a member 20 that defines a chamber 25. A pressure sensor 30 is placed in sensing communication with the member 20. As a result, changes in the external forces on the member 20 are detected as pressure changes within the chamber 25 by the pressure sensor 30.

To that end, the member 20 may be constructed of a compressible material including, but not limited to, nylon, vinyl, rubber, and similar materials. As an option, the member 20 may be constructed of a material that gives the member 20 a softness substantially equal to or less than that of the surrounding mattress material. When using a member 20 having a softness substantially equal to or less than the softness of the mattress, the therapeutic value of the mattress is improved because the member 20 will not create a pressure point in the mattress.

In general, the member 20 may be fluid-tight, but some fluid loss is permissible. As will be appreciated, changes in the chamber pressure caused by patient migration will still be detected by the sensor 30 even if a loss of fluid is occurring. If necessary, losses may be compensated for by periodically refilling the member 20 with fluid. To that end, an air supply, including, but not limited to a pump P (FIG. 8), may be fluidly connected to the member 20. When using a pump P, to minimize losses through the pump P, a valve V may be used to close off the pump P from the member 20 after the desired inflation of the chamber 25 is achieved.

Figure 3:
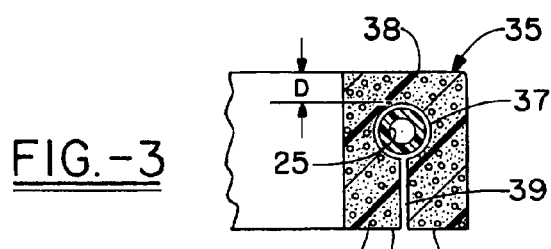
FIG. 3 is a partially fragmented partially sectional end view as might be seen along line 3-3 in FIG. 1.

The member 20 may be given any desired shape and may be of any suitable size. In the example shown in FIG. 1, a member having an elongate tubular shape is shown. As best shown in FIG. 3, the member 20 may have a circular cross-section. Returning to FIG. 1, member 20 may have a first end 21 and a second end 22 that are located on opposite sides of the mattress centerline C. While the ends 21,22 are shown at the lateral outward edges 23,24 of the mattress 12, it will be appreciated that the member 20 may be located at any position relative to the mattress 12. For example, as shown in FIG. 1, the member 20 may be located at the periphery 26 of the mattress 12, or as shown in FIG. 6, member 20 may be located at positions inboard of the mattress periphery 26. The ends 21, 22 or individual members 20, when multiple members 20 are used, may be arranged symmetrically about the mattress centerline C or in an unsymmetrical fashion.

Also, member 20 may have any length. For example, member 20 may extend the entire length of the mattress 12 or a selected portion of the mattress 12. For example, the member 20 may have a length that allows it to be adjacent to the patient's torso. Locating the member 20 at the upper end 14 of the mattress 12 near the patient's torso is believed to provide earlier detection of movement that might lead to a dangerous condition because the patient's torso is closest to the edge of the mattress 12. In the example shown in FIG. 1, the member 20 extends from one end of the mattress 12 to a point near or beyond the mattress's transverse center-line TC.

Alternatively, when used in connection with an articulating mattress, as shown for example in FIGS. 4-5A, that is hinged on an axis A, the member 20 may be located near or extend beyond the axis A to provide information relating to the incline of the mattress 12 as will discussed more completely below.

With reference to FIG. 1, the member 20 is placed in proximity to the patient, as by attaching the member 20 to the mattress 12. For purposes of this invention, "attachment" of the member 20 may include any mechanical attachment of the member 20 to the mattress 12, insertion of the member 20 within a receiver formed in the mattress 12 or an adjacent structure, or simply laying the member 20 on or beneath the mattress 12. As shown in FIG. 1, member 20 may also be attached by inserting the member 20 within a member support 35 that is attached to the mattress 12. In general, the member support 35 may be any member suitable for supporting the member 20. In the example shown, member support 35 is a bolster 36 that defines a receiver 37 for the member 20. The member support 35 may be constructed of materials commonly used to construct mattresses. For example, as shown in FIG. 3, the member support 35 may be constructed of foam.

In the example shown, member support 35 defines a cylindrical shaped receiver 37 at a depth D from the upper surface 38 of the member support 35. Depending on the material used to construct the member support 35 and the level of sensitivity desired, the depth D at which the receiver 37 is located may be increased or decreased.

Also, while the receiver may have a length corresponding to the portion of the migration sensor 15 that is inserted into the receiver 37, as shown, the support 35 may alternatively define a receiver 37 that extends the entire length L of the support 35. This provides flexibility in that the migration sensor 15 may be inserted at either end of the support 35 and facilitates the use of extrusion methods of forming the support 35. The support 35 allows forces to be transmitted from the patient to the migration sensor 15 and may be made flexible to facilitate the transmission of these forces.

As best shown in FIG. 3, to facilitate radial insertion of the migration member 20 when axial insertion is not possible, for example, when the receiver 37 does not open outward at an end of the support 35 or mattress 12 or simply to provide an alternative to axial insertion, the support 35 may be provided with a slot 39 that extends radially outward from the receiver 37. Legs 41 on either side of the slot 39 may be flexed outwardly to allow radial insertion of the member 20. In the example shown, the slot 39 extends downward from the receiver 37.

FIGS. 7 and 8 depict examples of members 20, but are not to be considered limiting. The member 20 may be made compressible as by having crushable zones or, as discussed above, by selecting a material that will deform under suitable force. As shown in FIGS. 7 and 8, a thin membrane may be used to construct the member 20. To increase the sensitivity of the member 20, as shown in FIG. 7, the member's chamber 23 may be filled with a porous material 40 including, but not limited to, foam. Alternatively, a pump P may be used to maintain the member 20 in an over inflated condition. A valve V may be used to close the conduit to the pump P to avoid fluid loss back through the pump P.

As mentioned, a sensor 30 is in sensing communication with member 20. To that end, member 20 may provided with an opening 28 that opens to the sensor 30. Other methods of sensing the pressure or changes in pressure within member 20 may be used as well. In the example shown in FIG. 1, a conduit 31 extends from member 20 to the sensor 30 to fluidly connect the member 20 to the sensor 30. As shown in FIG. 4, the member 20 may directly connect to the sensor 30 with the opening formed at the member's second end 22.

The sensor 30, in turn, communicates with a controller C, which monitors changes in the member's pressure and notifies the care giver. The term controller encompasses any device capable of receiving pressure information from the pressure sensor 30 and notifying the care giver. The controller C may be simple in the sense that any change in pressure is communicated to the caregiver by activating an alarm, described more completely below. In this example, the controller C acts much like a switch. Alternatively, the controller C may be programmable and include a processor and memory if necessary.

The controller C may be programmed with instructions to alert a care giver only under certain circumstances. For example, controller C may be programmed with a selected threshold pressure. The controller C may, then, compare the sensed pressure to the selected threshold pressure. In comparing the sensed pressure to the threshold pressure the controller C may warn the care giver in a variety of ways. In one example, the selected threshold is programmed to indicate a dangerous condition. If the controller C detects a pressure equal to or exceeding this pressure it may activate an alarm or otherwise communicates this condition to a care giver. Alternatively, the controller C may be programmed to incrementally alert the care giver as the sensed pressure approaches the threshold. Along these lines, the controller C may be programmed to signal the care giver with increasing frequency or intensity as the threshold is approached. Since some changes in pressure may be considered permissible, the controller C may be programmed with a base pressure value that must be exceeded before the controller C notifies the care giver. The controller C may notify the user by communicating an alarm signal to an existing system within the care giver facility, for example, a nurse call or similar system.

Notification may be in any perceptible form including for example, visual, audible, or tactile forms. For sake of simplicity, the device used to notify the caregiver will be referred to as an alarm AL. The alarm AL may form part of the controller C or, as shown in FIG. 6, may be separate from the controller C. Optionally, the alarm AL may be located remotely from the mattress 12, for example at a central care giver's station. The alarm AL may be mobile and carried by a care giver. Multiple alarms AL may be used together, as well. For example, the controller C may simultaneously signal an alarm within the controller C and a remote alarm AL. Any known device capable of receiving a signal from the controller C and notifying the care giver may be used as an alarm AL. Or, a custom alarm AL may be designed. In FIG. 6, communication between the controller C and alarm AL is schematically shown, and may occur in any manner including but not limited to electrical, optical, and wireless forms.

Alarm AL may be any suitable device for generating a perceptible form of notice. For example, alarm AL may include, but not be limited to, a speaker that generates an audible tone, bell, or recorded voice or other audible cue; a light, an LED, a display screen, or other viewable device; or a vibrating unit, Braille reader, or other tactile device.

As an alternative or in addition to the above described systems, controller C may be programmed, such that, at a selected pressure range corresponds to a selected risk level. Upon detecting pressures within the respective ranges, the controller C itself, or through alarm AL, notifies the care giver of the selected risk level. One example, which is not considered limiting, provides low, medium, and high risk levels associated with increasing pressure ranges. As a further alternative, the actual pressure value may be communicated to the care giver.

When communicating more complex information, the controller C or alarm AL will include a suitable audible, visual, or tactile device for communicating the risk level, such as those described above with respect to the alarm AL. Other examples, which are not considered limiting, would be visual displays or simply a "display", including, but not limited to, a numeric or alpha-numeric LED, series of lights associated with a printed scale, or a monitor.

Figure 4:
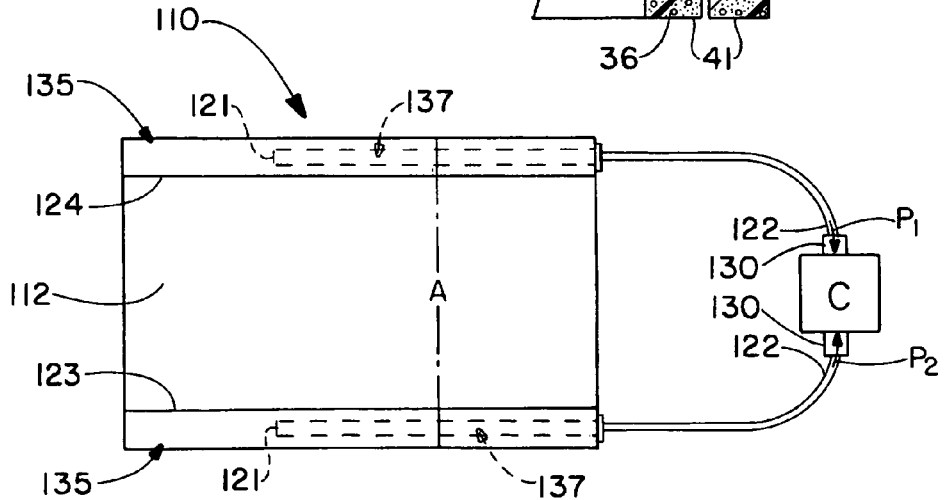
FIG. 4 is a patient migration monitor according to the concepts of the present invention having two migration sensors shown near the edges of a mattress having a first end insertable within the mattress for detecting patient movement and a second end connected to a sensor that detects changes in the internal pressure within the sensor and reports the same to a controller.

FIGS. 4-5A depict an alternate patient monitoring system, generally indicated by the number 110. Patient monitoring system 110 is similar to the system 10 and thus like numbers will be used to refer to like components. As shown in FIG. 4, system 110 differs from system 10 in that it includes multiple migration sensors, generally indicated by the number 115. As in the previous embodiment, each migration sensor 115 includes a member 120 that defines a chamber 125, and is in fluid communication with a sensor 130. In this embodiment, individual pressure changes within the members 120 may be independently sensed at multiple locations. In the example shown, a pair of members 120 is used, but any number of migration sensors 115 may be used. To that end, pressures $(P_1, P_2)$ are detected by a pair of sensors 130, which respectively report the pressures $(P_1, P_2)$ to controller C. By monitoring the changes in pressure at the individual member locations more information about the patient's movements may be defined. For example, in the embodiment shown, an increase in pressure in a single member could indicate which side of the mattress 112 the patient is moving toward. Also, detection of simultaneous changes in the pressures within individual members 120 may indicate that the angle of the mattress 112 is being changed ruling out a dangerous condition, as described more completely below. To avoid false alarms caused by changes in the mattress angle, controller C may be programmed to reset after the detection of simultaneous pressure changes in separate migration sensors 115 located on opposite sides of the mattress 112. For example, upon detecting such changes in pressure, the controller C may be programmed to zero the pressure values detected at the simultaneously changing migration sensors 115 to filter out pressure changes not associated with the patient.

In the example shown, one migration sensor 115 is located at each lateral outward extremity 113 of mattress 112. As discussed in the previous embodiment, the migration sensor 115 may be incorporated as part of the mattress 112 or be separately attached. In the latter case, a migration sensor support, generally indicated by the number 135, may be provided and attached or positioned adjacent the mattress 112 in any known manner, for example, snaps, Velcro, buttons, or other mechanical fasteners, or adhesives, welds, and the like. Support 135 may be similar to the support 135 described above and include an elongate member that defines a receiver 137 adapted to receive the migration sensor 115. While the receiver 137 may have a length corresponding to the portion of the migration sensor 115 that is inserted into the receiver 137, the support 135 may define a receiver 137 that extends the entire length of the support 135. This provides flexibility in that the migration sensor 115 may be inserted at either end of the support 135 and facilitates the use of extrusion methods of forming the support 135. The support 135 allows forces to be transmitted from the patient to the migration sensor 115 and may be made flexible to facilitate the transmission of these forces. In the example shown, support 135 is constructed of foam. As discussed, the type of support material or depth D at which the receiver 137 is located may be altered to increase or decrease the migration sensor's sensitivity to the patient's movement.

In the depicted example, members 120 are used in connection with an articulating mattress 112. The articulating mattress 112 folds or bends along an axis A. It will be appreciated that in some mattresses more than one axis may be provided. The length and position of the migration sensor 115 may be adjusted to compensate for pressure changes along these axes in the same manner as the single axis case described below. With plural migration sensors 115, articulation of the bed or mattress 112 may be detected as a pressure change within migration sensors 115 located on opposite sides of the mattress 112. As shown in FIG. 5A, the change in the mattress 112 angle α causes the member 120 to bend at an (β) or otherwise compresses the member 120 near the axis A. In contrast to a patient rolling toward the edge of the mattress 112, compression caused by a change in the mattress angle, will be detected on opposite sides of the mattress 112. It will be appreciated that the pressure change will be detected by both migration sensors 115 at roughly the same time. It is foreseeable that the pressure changes at each migration sensor 115 may not occur exactly at the same time. Consequently, reference to this condition as a "substantially simultaneous" change in pressure at plural migration sensors 115 will be understood as including pressure changes that occur exactly at the same time or with some delay between the detected pressure changes at plural migration sensors 115. In detecting these changes, the goal is to rule out false alarm conditions. To that end, the controller C may be programmed with a permissible delay between pressure readings at plural migration sensors 115 as indicative of a change in mattress angle, for example, 5 seconds. This example is not limiting, as the care giver may enter any time period that it deems to be a safe window for the controller C to rule out conditions that might create a false alarm.

To avoid a false alarm, upon detecting a substantially simultaneous change in pressure at plural migration sensors 115 located on opposite sides of the center line CL, controller C may be programmed to automatically recalibrate itself to zero pressure so that a false alarm is not triggered. If the condition triggering the substantially simultaneous pressure changes is ongoing, for example, the mattress angle is being changed over a period of time, the controller may be programmed to continue to recalibrate to zero until the substantially simultaneous change in pressures at plural migration sensors 115 ends.

Alternatively, the controller may be programmed to alert the caregiver that the patient is changing the angle of the mattress 112 or otherwise provide notice that would cause the caregiver to investigate the patient's status without indicating an immediately dangerous condition. Since the pressure changes caused by changing the mattress angle are expected to be roughly the same, despite the simultaneous change in pressure at each migration sensor 115, the controller C may still notify the care giver of a dangerous condition if the pressures at each migration sensor 115 are different.

FIG. 6 schematically depicts a patient monitoring system, generally indicated by the number 210, where the receivers 237 are formed within the mattress 212, and the members 220 are inserted therein. Members 220 could also be placed beneath the mattress 212 in the same configurations. In the example, a single member 220 having four ends is used. Alternatively, as described with respect to system 110, multiple members 220 may be used each separately communicating with the controller C.

FIG. 6 also depicts an example of a transversely extending member 220A, which like the previously described member 220, may be placed within a transverse receiver 237A. While shown near the foot of the mattress 212, the transverse member 220A may be located at any point along the length of the mattress 212. Member 220A, while not particularly suited for detecting rolling movement of the patient, may be used to detect pressure changes in local areas on the mattress. For example, member 220A may be used to detect a patient exiting the mattress 212, which might be seen as the pressure being removed from member 220A. A sharp increase in pressure followed by its release might also indicate that a patient has exited the mattress 212. Controller C may be programmed to detect such conditions at member 220A and notify the care giver, as described in the previous embodiments.

While a full and complete description of the invention has been set forth in accordance with the dictates of the patent statutes, it should be understood that modifications can be resorted to without departing from the spirit hereof or the scope of the appended claims.

What is claimed is:

1. A system for monitoring patient migration on a mattress, the system comprising: plural migration sensors, each migration sensor including a compressible member defining a chamber at least partially filled with fluid, and a pressure sensor in sensing communication with said member; a controller in communication with each pressure sensor, wherein said controller receives a pressure value from said pressure sensor and stores said pressure value in a memory, said controller upon detecting a substantially simultaneous change in the pressure values reported from compressible members on opposite sides of the mattress, being adapted to zero said pressure values in memory.

2. A system for monitoring patient migration used in combination with a mattress, the mattress comprising:
    a center-line, said mattress being pivotable about an axis that is transverse to said center-line; and
    said system comprising plural migration sensors extending parallel to said center-line and located on opposite sides thereof; said migration sensors each include a compressible member defining a chamber at least partially filled with fluid, and a pressure sensor in sensing communication with said compressible member adapted to detect a pressure within said compressible member; and a controller in communication with each of said pressure sensors and adapted to receive said pressure from said pressure sensors, wherein said controller is adapted to compare said pressures from each of said migration sensors, and upon detecting a substantially simultaneous change in pressure in at least two migration sensors located on opposite sides of said center-line of said mattress, the controller automatically calibrates itself to zero until the substantially simultaneous change is no longer detected.

* * * * *